United States Patent [19]

Koutantzis

[11] Plant 4,337

[45] Nov. 28, 1978

[54] AFRICAN VIOLET NAMED PINK ULLI

[75] Inventor: Konstantinos I. Koutantzis, West Chicago, Ill.

[73] Assignee: Pan American Plant Company, West Chicago, Ill.

[21] Appl. No.: 876,278

[22] Filed: Feb. 9, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Chas. W. Rummler

[57] ABSTRACT

A new variety of African violet plant for potted plant culture particularly distinguished by its year around blooming capability, its profuse production of large medium pink flowers, and its compact growth with abundant foliage having leathery leaves of a solid dark green color on the upper side which provide a spreading base and attractive contrast for clusters of pink blossoms.

3 Drawing Figures

BACKGROUND OF THE NEW PLANT

This new variety of African violet plant was discovered by me in 1976 as a sport of the variety Ulli (U.S. Plant Pat. No. 3,807) under culture at West Chicago, Ill. The medium pink flower color compared with that of its parent caused me to reproduce this sport by cuttings from the original plant at West Chicago, Ill., and subsequent propagation of the new plant by means of leaf cuttings at West Chicago, Ill., and at Parrish, Fla., has demonstrated that its distinctive characteristics hold true from generation to generation and appear to be firmly fixed.

DESCRIPTION OF THE DRAWINGS

This new variety of African violet plant is illustrated by the accompanying drawings, of which sheet one is a full color photographic view of the plant in full bloom, the colors shown being as nearly true as it is reasonably possible to obtain by conventional photographic procedures; sheet two is a mechanical print showing the top side of representative leaves of the new variety; and sheet three is a similar print showing the under side of the leaves shown on sheet two.

DESCRIPTION OF THE NEW PLANT

The following is a detailed description of my new African violet plant with the color designations being according to the R.H.S. Colour Chart published by The Royal Horticultural Society of London, England, with collaboration by The British Colour Council.

THE PLANT

Origin: Sport.
Parentage: Ulli (U.S. Plant Pat. No. 3,807).
Classification:
*Botanic.*—*Saintpaulia ionantha.*
*Commercial.*—African Violet.
Form: Compact potted plant.
Height: 9 to 11 cm. from base to top of flowers.
Growth: Condensed and vigorous with sturdy upright flower peduncles and fairly strong petioles which tend to spread horizontally.
Foliage: Abundant in quantity.
*Size of leaf.*—About 6.8 to 9.4 cm. long and about 6.2 to 8.1 cm. wide. Shape: Ovate to orbicular with crenate margins. Texture: Tomentose and leathery. Aspect: Pubescent.
*Ribs and veins.*—Pinnate and very pronounced on under side of leaf.
*Color.*—Upper Side — 147A. Under Side — 157A.
*Petioles.*—Length — About 3.6 to 9.7 cm. Strong and generally horizontally spreading.

THE BUD

Form: Ovoid; generally globular becoming urn-shaped as it opens.
Size:
*Diameter.*—About 5 to 9 mm.
*Depth.*—About 0.96 to 1.0 cm.
Opening rate: Very slow. Five weeks from visible bud to opening of the flower.
Color:
*When sepals first divide.*—186C, 186D.
*When petals begin to unfurl.*—186D.
Sepals: Enclose bud for a very short period.
*Form.*—Spear-shaped and upstanding.
*Color.*—Inside — 148A. Outside — 147B, 148A.
Calyx: Funnel-shaped and synsepalous.
*Splitting.*—Splits to star-shape.
*Aspect.*—Inside — Smooth. Outside — Hairy.
Peduncle: Length — About 2.5 to 3.7 cm.
*Strength.*—Strong and erect.
*Texture.*—Hairy.
*Color.*—183A.

THE FLOWER

Blooming habit: Recurrent profusely the year around.
Borne: In clusters. The inflorescence is a cyme.
Size of flower: Large. Diameter — About 3.8 to 5.4 cm.
Shape of flower: Cup-shaped when first opening becoming quite flat when mature.
Petalage: Five petals, three being larger than the other two.
*Arrangement.*—Synpetalous.
*Form.*—Rotate, with bilateral symmetry and wavy margins.
*Texture.*—Soft.
*Appearance.*—Glittering on upper surface. Satiny on under side.
*Color.*—Upper Side — 74C, 74D. Under Side — 74D. Tonality at 2 Meters: 73B.
Peduncle: Length — Main stem about 5.2 cm.

*Strength.*—Sturdy and upright.
*Color.*—183A.
Pedicels: About 2.5 to 3.7 cm. long.
*Character.*—Upright and strong.
Discoloration: The color has a tendency to fade upon aging after full bloom.
Persistence: The flowers hang on and dry.
Effect of weather: Hot weather suppresses flowering and fades the color. The plants thrive best in relatively high humidity.
Fragrance: None.
Lasting quality: 10 to 14 days for the fully opened flowers. Not recommended as cut flower.

REPRODUCTIVE ORGANS

Stamens: Anthers — Basifixed and about 3 mm. long.
*Filaments.*—Length — About 6 mm. Color: 78B.
*Pollen.*—color — White.
Pistils: Number — One.
*Style.*—About 8 mm. long.

*Stigma.*—Color — 78B.
Ovaries: Superior and tomentose.

This variety of African violet plant is particularly distinguished by the medium pink color of its flowers when compared with its parent Ulli (U.S. Plant Pat. No. 3,807) and by the profuse production of blossoms on strong erect stems which extend above abundant horizontally spreading, dark green foliage which provides a sharply contrasting background for the mass of pink blooms. The plant is very well suited for potted plant culture and its year around blooming capability gives the plant a commercially attractive value.

I claim:

1. A new variety of African violet plant, substantially as herein shown and described, characterized by its profuse production of medium pink blossoms clustered above abundant horizontally spreading, dark green foliage and by its year around blooming capability.

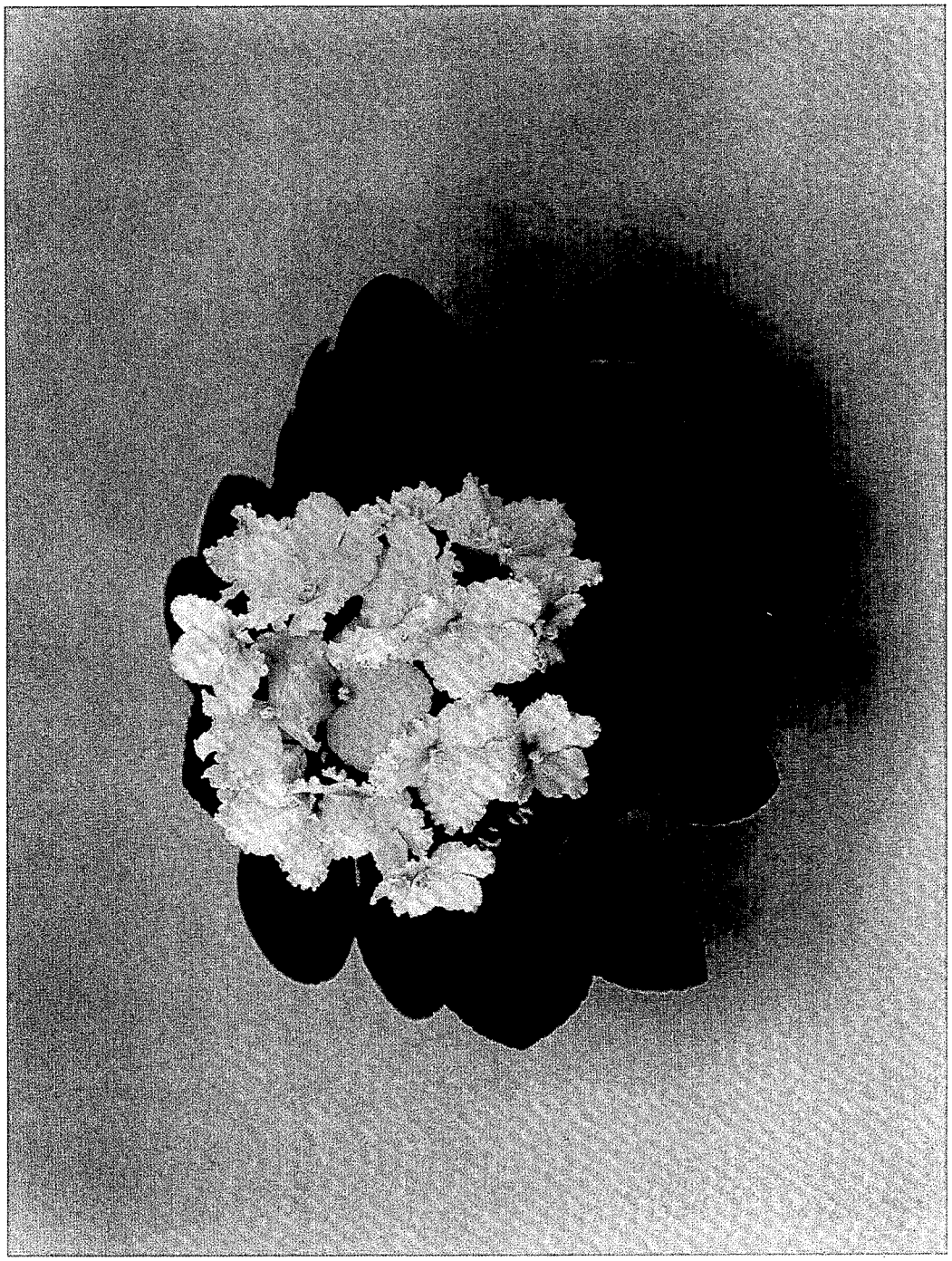

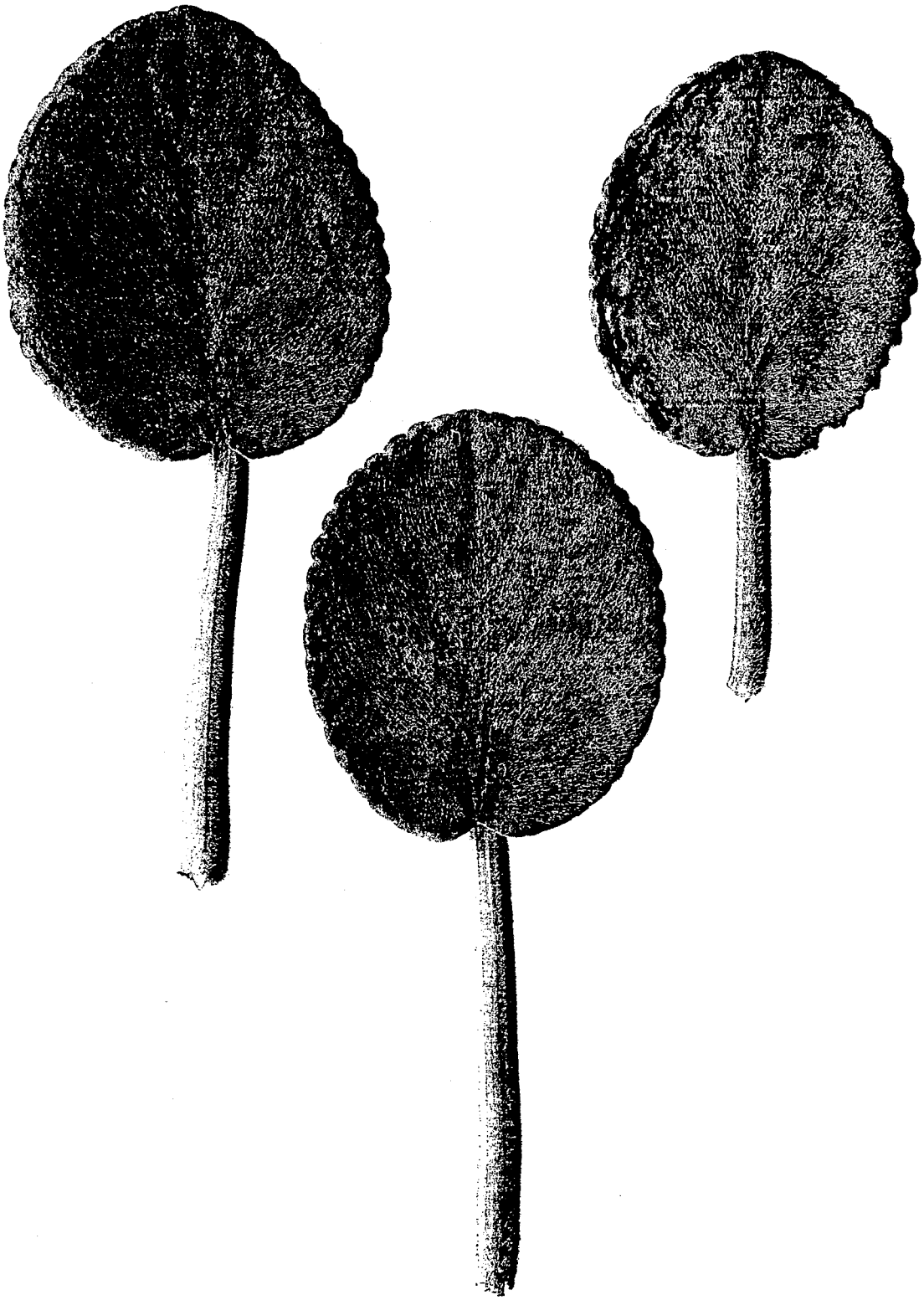

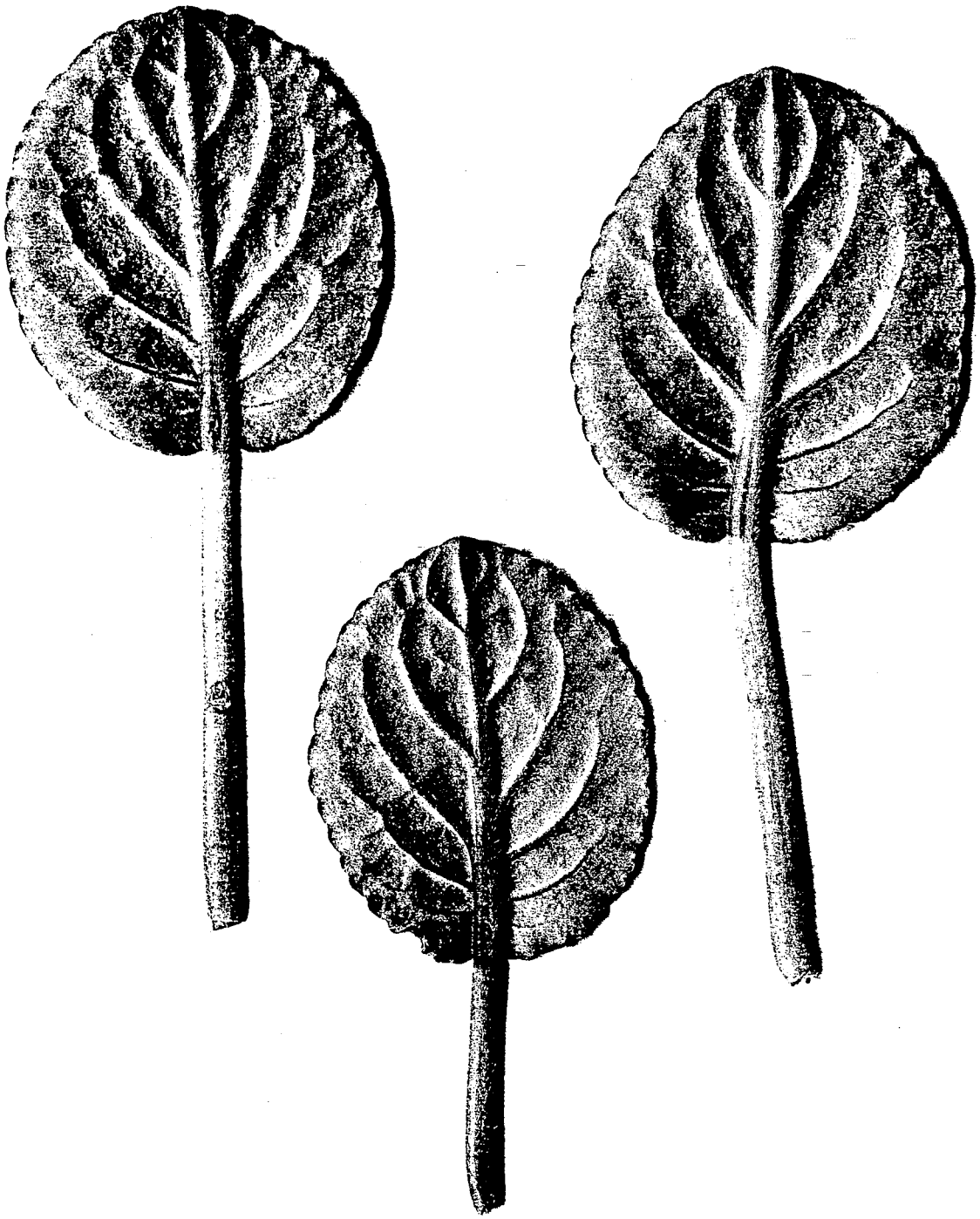

* * * * *